US010827598B2

(12) United States Patent
Vioel et al.

(10) Patent No.: US 10,827,598 B2
(45) Date of Patent: Nov. 3, 2020

(54) PLASMA GENERATOR MODULE

(71) Applicant: DBD Plasma GmbH, Goettingen (DE)

(72) Inventors: Wolfgang Vioel, Adelebsen (DE);
Stephan Wieneke, Goettingen (DE);
Alexander Gredner, Friedland (DE);
Daniel Freier, Bovenden (DE)

(73) Assignee: DBD PLASMA GMBH, Goettingen (DE)

( * ) Notice: Subject to any disclaimer, the term of this patent is extended or adjusted under 35 U.S.C. 154(b) by 0 days.

(21) Appl. No.: 16/790,982

(22) Filed: Feb. 14, 2020

(65) Prior Publication Data
US 2020/0187342 A1    Jun. 11, 2020

Related U.S. Application Data

(63) Continuation-in-part of application No. PCT/EP2018/071517, filed on Aug. 8, 2018.

(30) Foreign Application Priority Data

Aug. 16, 2017 (DE) ........................ 10 2017 118 652

(51) Int. Cl.
*H05H 1/24* (2006.01)
(52) U.S. Cl.
CPC ... *H05H 1/2406* (2013.01); *H05H 2001/2412* (2013.01)
(58) Field of Classification Search
None
See application file for complete search history.

(56) References Cited

U.S. PATENT DOCUMENTS 7,989,034 B2    8/2011  Prinz et al.
9,443,702 B2 *  9/2016  Savas .................... C23C 16/24
(Continued)

FOREIGN PATENT DOCUMENTS

CN      204 598 448 U       8/2015
DE      10 2005 029 360 A1  12/2006
(Continued)

OTHER PUBLICATIONS

J. Ehlbeck et al.: Low Temperature Atmospheric Pressure Plasma Sources for Microbial Decontamination, Journal of Physics D: Applied Physics, IOP Publishing, 2011, 44 (1), pp. 13002 (https://hrl.archives-ouvertes.fr/hal-00585169).

(Continued)

*Primary Examiner* — Minh D A
*Assistant Examiner* — James H Cho
(74) *Attorney, Agent, or Firm* — Thomas | Horstemeyer, LLP

(57) ABSTRACT

In an array of a plurality of plasma generator modules for generating a physical plasma by dielectric barrier discharges at atmospheric pressure, each of the plasma generator modules comprises two parallel electrodes linearly extending at a lateral distance, one of which having a dielectric barrier; connection devices for connecting the electrodes to a high voltage source; two flat gas-conducting elements conducting a working gas between the electrodes; and a module housing delimiting the respective plasma generator module laterally along the electrodes and transversely to the electrodes. The module housings are fixed to one another or to a common module frame by means of fixation devices. The module housings are arranged side by side both in a first direction along and in a second direction transverse to the electrodes, and in such an offset way that the electrodes of the plasma (Continued)

generator modules partially overlap in the direction along the electrodes.

20 Claims, 9 Drawing Sheets

(56) References Cited

U.S. PATENT DOCUMENTS

| | | | |
|---|---|---|---|
| 10,143,510 B2 | 12/2018 | Nettesheim et al. | |
| 2006/0196424 A1* | 9/2006 | Swallow | H05H 1/46 118/723 E |
| 2008/0061035 A1 | 3/2008 | Kim | |
| 2009/0200948 A1* | 8/2009 | Selwyn | H05H 1/2406 315/111.21 |
| 2010/0112235 A1* | 5/2010 | Prinz | H05H 1/2406 427/569 |
| 2010/0175987 A1* | 7/2010 | Creyghton | H05H 1/2406 204/164 |
| 2015/0069911 A1 | 3/2015 | Nettesheim et al. | |

FOREIGN PATENT DOCUMENTS

| | | |
|---|---|---|
| DE | 10 2008 018 827 A1 | 3/2015 |
| DE | 10 2013 109 887 A1 | 3/2015 |
| DE | 10 2013 113 941 A1 | 6/2015 |
| EP | 1 767 068 A2 | 3/2007 |
| GB | 2551890 A | 1/2018 |
| JP | 2003 338399 A | 11/2009 |
| KR | 101 709 167 B1 | 2/2017 |
| WO | 0154464 A1 | 7/2001 |
| WO | 2010083040 A1 | 7/2010 |
| WO | 2011095245 A1 | 8/2011 |
| WO | 2014093513 A1 | 6/2014 |
| WO | 2015164760 A1 | 10/2015 |

OTHER PUBLICATIONS

International Preliminary Report on Patentability in co-pending, related PCT Application PCT/EP2018/071517, dated Feb. 28, 2020.

* cited by examiner

PLASMA GENERATOR MODULE

CROSS REFERENCE TO RELATED APPLICATIONS

This application is a continuation in part to International Application PCT/EP2018/071517 with an international filing date of Aug. 8, 2018 entitled "Plasma generator module and use thereof" and claiming priority to co-pending German Patent Application No. DE 10 2017 118 652.2 entitled "Plasmageneratormodul and dessen Verwendung" and filed on Aug. 16, 2017.

FIELD OF THE INVENTION

The present invention generally relates to generating a physical plasma. More particular, the present invention relates to a module array including a plurality of plasma generator modules configured for generating the physical plasma by dielectric barrier discharges at atmospheric pressure. Even more particularly, each of the plasma generator modules of the module array comprises two linearly extending electrodes extending parallel to each other at a lateral electrode distance, at least one of the two linearly extending electrodes being provided with a dielectric barrier; connection devices configured for connecting the electrodes to a high voltage source; two flat gas-conducting elements configured for conducting a working gas between the electrodes; and a module housing delimiting the respective plasma generator module laterally along the electrodes and transversely to the electrodes.

BACKGROUND OF THE INVENTION

J. Ehlbeck et al.: Low Temperature Atmospheric Pressure Plasma Sources for Microbial Decontamination, Journal of Physics D: Applied Physics, IOP Publishing, 2011, 44 (1), p. 13002 disclose different arrangements of electrodes for dielectric barrier discharges of different discharge forms, which are caused by applying an alternating high voltage at atmospheric pressure and which generate a physical plasma. These different discharge forms include a direct dielectric barrier discharge between an electrode and an object connected to electric earth, wherein the alternating high voltage applied to the electrode is generated with regard to electric earth, a dielectric barrier discharge between two electrodes, between which the alternating high voltage is applied, the plasma generated in this way being blown out as a plasma jet, and a coplanar sliding discharge between a first electrode and an object as well as between the object and a second electrode, the alternating high voltage also being applied between the electrodes but a direct dielectric barrier discharge between the electrodes being avoided, for example, by means of a screen of a dielectric arranged between the electrodes.

Depending on the microbial contamination to be eliminated or the object contaminated, one or the other discharge form may be particularly well suited for generating the decontaminating plasma.

Further, the treatment of large area objects may make it necessary to use large electrodes to generate the physical plasma over a large area. Here, it proves to be difficult to cause the dielectric barrier discharge uniformly over all parts of the large electrodes.

A cold plasma device for killing germs on food stuff which includes both an electrode arrangement for a sliding discharge and an electrode arrangement for a plasma jet is known from international application publication WO 2014/093513 A1.

A plasma generator for generating a plasma jet, whose electrode arrangement may also be used for generating a direct dielectric barrier discharge with regard to an object to be treated, is known from international application publication WO 2011/095245 A1.

International application publication WO 2015/164760 A1 describes a treatment or disinfection of flowing water by means of a discharge generating a physical plasma. The discharge generating ozone is caused by a Marx high voltage generator. This high voltage generator includes a row of electrode pairs connected in parallel, to ignite a corona discharge in a plasma chamber. Here, the distance of the electrodes of each electrode pair, which shall be about 15 to 40 mm, is adjustable.

International application publication WO 01/54464 A1 discloses a three phase plasma jet generator with adjustable electrodes for generating a hot plasma jet. The electrodes are adjustable to keep constant a distance and a configuration of the electrodes even with occurring wear of the electrodes.

International application publication WO 2010/083040 A1 discloses a method and an apparatus for continuously producing nano and micro particles like, for example, colloids in liquid solutions. The particles are produced by means of an adjustable plasma and an adjustable electrochemical production method in a liquid like, for example, water, which is used as an active dielectric. For adjusting the plasma, a vertical height of electrodes above a surface of the liquid is adjustable.

CN utility model CN 204 598 448 U discloses a remote controlled adjustment device by which a distance of electrodes is adjustable in an apparatus for generating a physical plasma by a dielectric barrier discharge of a fixed discharge form.

US patent application publication 2008/0061035 A1 discloses a plasma generator in which the distance of electrodes is adjustable, the electrodes being mounted to gas conducting elements, arranged parallel to one another and alternately connected to the two poles of an alternating high voltage source. For adjusting their distance, the electrodes are moved towards each other transversely to their directions of main extension together with the gas conducting elements.

An apparatus for generating a plasma or an excited gas or gas mixture for treatment of wounds is known from German patent application publication DE 10 2013 113 941 A1 corresponding to U.S. Pat. No. 10,143,510 B2. The apparatus includes an expansion element which encloses the wound area to be treated with its distal end. The proximal end of the expansion element is releasably connected to a housing of the apparatus at an opening, out of which the generated plasma or excited gas or gas mixture emerges. A piezoelectric transformer integrated in the housing of the known apparatus is provided as a high voltage source. The truncated cone shaped expansion element has openings. A feedback by means of an integrated pump leads gas out of the interior of the expansion element into the area of the high voltage end of the piezoelectric transformer.

There still is a need of a module array of plasma generator modules for generating a physical plasma by dielectric barrier discharges at atmospheric pressure, which allows for a stable and secure operation for treating even very large area objects with a physical plasma.

SUMMARY OF THE INVENTION

The present invention relates to module array including a plurality of plasma generator modules configured for generating a physical plasma by dielectric barrier discharges at atmospheric pressure. Each of the plasma generator modules comprises two linearly extending electrodes extending parallel to each other at a lateral electrode distance. At least one of the two linearly extending electrodes is provided with a dielectric barrier. Each of the plasma generator modules further comprises connection devices configured for connecting the electrodes to a high voltage source; two flat gas-conducting elements configured for conducting a working gas between the electrodes; and a module housing delimiting the respective plasma generator module laterally along the electrodes and transversely to the electrodes. The module housings of the plasma generator modules of the plurality of plasma generator modules are each provided with fixation devices and fixed to one another or to a common module frame by means of their fixation devices. The module housings of the plasma generator modules of the plurality of plasma generator modules are arranged side by side both in a first direction along and in a second direction transverse to the electrodes of the plurality of plasma generator modules, and in such an offset way that the electrodes of the plurality of plasma generator modules partially overlap in the direction along the electrodes.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
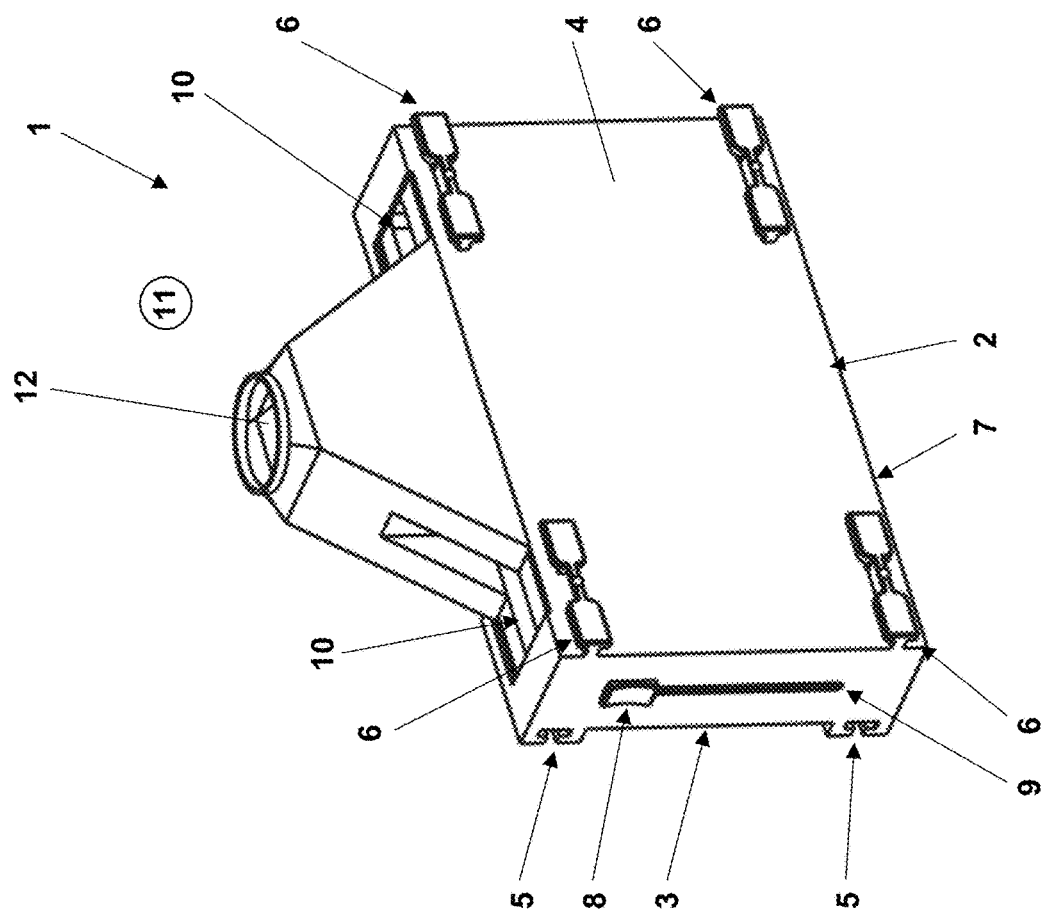
FIG. 1 is a perspective view of a plasma generator module of a module array of the present invention.

A module array according to the invention comprises a plurality of plasma generator modules for generating a physical plasma by dielectric barrier discharges at atmospheric pressure. Each of the plasma generator modules comprises two linearly extending electrodes. At least one of these two electrodes is provided with a dielectric barrier. The two electrodes are parallel to each other, and they are arranged at a lateral electrode distance. Each of the plasma generator modules further includes connection devices for connecting its electrodes to a high voltage source and two flat gas conducting elements for conducting a working gas between the electrodes.

Adjacent to at least one of the two electrodes of each plasma generator module, at its outside facing away from the other electrode, a slit-shaped entrance of a suction channel may be provided. At an outside of that gas conducting element connecting to the at least one of the two electrodes, the suction channel extends over this gas conducting element.

Via an area in front of the electrodes, the suction channel connects to a gas supply channel elongated by the gas conducting elements. Thus, the suction channel can be used to purposefully cause a stream of gas out of the gas supply channel through this area in front of the electrodes, in which a plasma treatment by means of the plasma generator module typically occurs. This stream of working gas ensures that a desired composition of the working gas is maintained despite the chemical reactions taking place in the plasma. Further, it is avoided that reaction products get out of the plasma into the surroundings of the plasma generator module in an uncontrolled way. Even further, the stream of gas around the electrodes of the plasma generator module into the suction channel provides a continuous cooling of the electrodes and their dielectric barriers.

A suction device comprising a fan or ventilator may be connected to the suction channel. Working gas conducted by the gas conducting elements, getting between the electrodes and passing through the electrode distance enters from there into the slit-shaped entrance of the suction channel around the at least one of the two electrodes, when the working gas is sucked off by the suction device through the suction channel.

The working gas of the plasma generator module may be air. The air may enter between the gas-conducting elements out of the surroundings of the plasma generator module through an embodiment of the gas supply channel beginning at that side of the plasma generator module facing away from its electrodes. Entering of the air into the gas supply channel may be caused by actively sucking the air through the suction channel laterally adjacent to the at least one of the electrodes by means of the suction device.

The suction device may be centrally provided for several of the plasma generator modules or all of the plurality of plasma generator modules of the entire module array. Alternatively, each individual plasma generator module may have such an own suction device. The suction device may be provided as a replaceable unit, which is, for example, connected to the suction channel via a plug-in connection. Further, a sensor unit for monitoring certain contents of the sucked off gas, i.e. of the sucked off air, may be provided either centrally or at each plasma generator module. The sensor unit may be connected to a central evaluation unit which may, for example, decide whether the sucked off gas may be released directly or has to be cleaned before it may be released.

In an embodiment of the plasma generator module with adjustable electrode distance, at least one of the electrodes is mounted to a first end of one of the two gas conducting elements such that the at least one of the two electrodes, together with the first end of the one of the two gas conducting elements, can be moved with regard to the other of the two electrodes and the other of the two gas conducting elements in the direction of the electrode distance. In this way, the electrode distance can be adjusted to different values for causing the dielectric barrier discharges in geometrically different discharge forms.

In this embodiment of the plasma generator module with adjustable electrode distance, an adjustability of the lateral electrode distance is given such that, by using the same electrodes, suitable conditions can be provided for causing the dielectric barrier discharges in geometrically different discharge forms. The gas conducting elements for conducting the working gas between the electrodes are also modified as the at least one of the electrodes is moved together with the one of the two gas conducting elements. All this is achieved simultaneously in that the at least one of the two electrodes is mounted to the lower end of the one of the two gas conducting elements and moved together with this gas conducting element with regard to the other of the two electrodes and the other of the two gas conducting elements.

It is to be understood that not only one but both electrodes may each be provided with a dielectric barrier in the plasma generator module. This may particularly mean that the electrodes are directly enclosed by a dielectric. Similarly, preferably both electrodes are each mounted to a first end of one of the two gas conducting elements in such a way that both electrodes, together with the first end of the respective gas conductive elements, are movable in the direction of the electrode distance.

In this embodiment of the plasma generator module with adjustable electrode distance, the movability of the respective electrode may be realized in that the gas conducting element, with its second end facing away from its first end, is mounted to a base structure of the plasma generator module via a one-axis swivel bearing. Alternatively, the gas conducting element may be rigidly connected to the base structure and provide a one-axis solid body joint. In any case, the electrode, together with the first end of the gas conducting element, can be swiveled with regard to the base structure about the swivel bearing or the solid body joint, respectively.

With the upper ends of the gas conducting elements being spatially fixed at the base structure of the plasma generator module, the gas supply channel supplying the working gas and spatially fixed with regard to the base structure may open between the two gas conducting elements.

For the purpose of moving the electrodes with regard to each other in the embodiment of the plasma generator module with adjustable electrode distance, two sliders may engage side edges of the gas conducting elements to which the movable electrodes are mounted. With sliding the sliders along a guide or guidance extending transversely to the electrodes, these sliders may alter the electrode distance. When both electrodes are movable with regard to the base structure, the sliders may engage both gas conducting elements, and the sliders may be slid in a main direction extending in the middle between the gas conducting elements.

If the plasma generator module has an additional dielectric screen which can be transferred out of an inactive position, in which it is located between the gas conducting elements, into an active position, in which it is located between the electrodes, and back, this dielectric screen may be coupled to the sliders in the embodiment of the plasma generator module with adjustable electrode distance. This means, that with shifting or sliding the sliders towards the electrodes, the dielectric screen is moved between the electrodes.

In an embodiment of the plasma generator module, the high voltage source is part of the plasma generator module. Particularly in the embodiment of the plasma generator module with adjustable electrode distance, this high voltage source may be switchable between different operation modes in which it applies different alternating high voltages to the electrodes for generating the geometrically different discharge forms. Connecting the high voltage source of the plasma generator module to an external voltage source may then, when the external voltage source is a low voltage source, be advantageously accomplished using low voltage connectors and lines only. This means that the parts of the module array, at which the high voltage is present, are limited to such areas of the plasma generator module, which can be easily defined and isolated. This would be much more complex with an external high voltage supply.

The high voltage source may particularly be provided at the plasma generator module as a replaceable unit. Such a replaceable unit allows, for example, for being replaced by another unit with higher maximum voltage or higher maximum electric power.

Laterally along and transversely to the electrodes, the plasma generator module is delimited by a module housing. Further, this module housing will be provided with fixation devices. These fixation devices may be provided at lateral walls of the module housing running along the electrodes of the plasma generator module. The module housing delimits the plasma generator module sideways in a defined way, and it provides the option to couple several plasma generator modules along and transversely to the electrodes in the module array.

Particularly, several or a plurality of plasma generator modules can be fixed by means of their fixation devices at one another or at a common module frame. In this way, the size of the area of an object which is subjected to a plasma treatment by means of the module array according to the invention in a certain period of time will be multiple times larger than the area which could be treated with only one the plasma generator modules within the same period of time.

Using the array module according to the invention, there is no danger that the treatment is unintentionally different in different parts of the treatment area, because each plasma generator module works and provides the physical plasma independently of its neighboring plasma generator modules. For this reason, the different plasma generator modules of the module array may generate different plasmas by geometrically different discharge forms of the dielectric barrier discharges. This particularly applies to the embodiment of the plasma generator module with adjustable electrode distance. In this case, all plasma generator modules may even be of equal design and nevertheless generate plasmas of different discharge forms.

When using the plasma module according to the invention, different values of the electrode distance may be adjusted for providing geometrically different discharge forms spatially side by side. In the embodiment of the plasma generator module with adjustable electrode distance, different values of the electrode distance may also be adjusted in a same plasma generator module one after the other temporally. The different discharge forms particularly include direct dielectric barrier discharges between the two electrodes, on the one hand, and an object located opposite to the electrodes, on the other hand, direct dielectric barrier discharges right between the two electrodes, the plasma generated by the dielectric barrier discharge being blown out onto an object positioned opposite to the electrodes, and direct dielectric barrier discharges and coplanar sliding or surface discharges between one of the two electrodes and an electrically conductive object located opposite to the electrodes as well as between this object and the other of the two electrodes of the respective plasma generator module. Whether the discharge form will be a direct dielectric barrier discharge or a coplanar sliding or surface discharge between one of the two electrodes and an electrically conductive object located opposite to the electrodes as well as between this object and the other of the two electrodes of the respective plasma generator module in the latter case may depend on the electric conductivity of the respective object.

The high voltage source may be operated in different operation modes for the different discharge forms. In case of a direct dielectric barrier discharge between both electrodes and the object, a same alternating high voltage with regard to the object or electric earth may be applied to both electrodes. In all other cases, an alternating high voltage may be applied between the two electrodes, i.e. in case of a plasma jet, a coplanar surface discharge and a direct dielectric barrier dischargers, in which the electrically conductive object serves as an intermediate electrode between the two electrodes of the respective plasma generator module.

The term alternating high voltage is to be interpreted quite broad here. Particularly, it includes temporal courses of the voltage applied consisting of short time voltage pulses or asymmetric voltage courses.

Which temporal course of the alternating high voltage is particularly suitable for which of the different discharge forms and which exact electrode distances are suitably adjusted for which of the different discharge forms is generally known to one skilled in the art. Nevertheless, one skilled in the art may simply adjust these values by a trial and error process in operating the plasma generator module.

Now referring in greater details to the drawings, the plasma generator module 1, which is depicted in FIG. 1 in a perspective view, comprises a module housing 2. Side walls 3 and 4 of the module housing 2 are provided with complementary fixation devices which are configured for coupling a plurality of same plasma generator modules 1 together. At an underside 7 of the housing 2, two electrodes are arranged, which are not visible in FIG. 1 and whose lateral electrode distance is adjustable by means of two sliders 3. The two sliders 3, of which only one is visible in FIG. 1, are vertically guided in slit-shaped guides or guidances 9 provided in the housing 2. At the upper side of the housing 2, a gas supply channel 10 enters into the module housing 2 at two points. Via the gas supply channel 10, air out of the surroundings 11 is sucked into the module housing 2. This sucking-in is effected via a suction channel 12, when a suction device, which is not depicted in FIG. 1, is connected to the suction channel 12.

Figure 2:
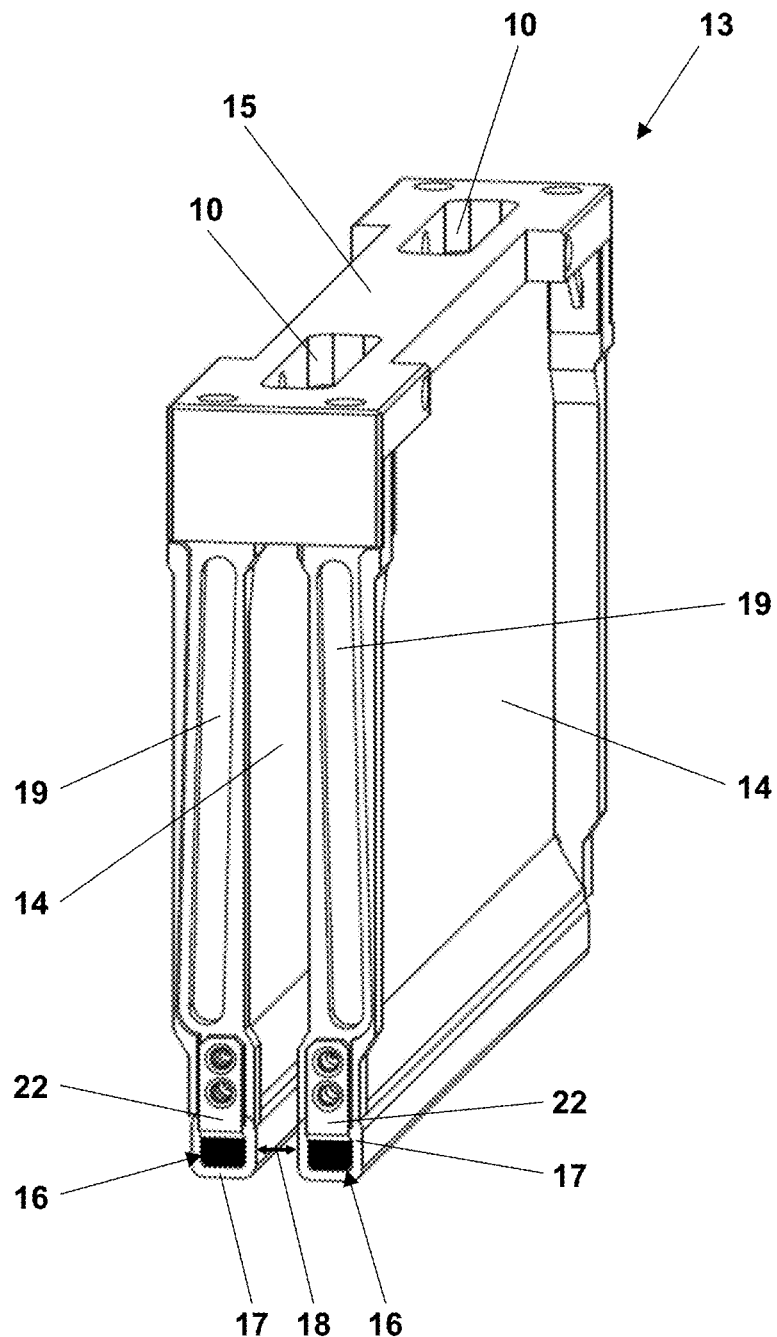
FIG. 2 is a perspective view of a component assembly of the plasma generator module according to FIG. 1.

FIG. 2 shows a component assembly 13 of the plasma generator module 1 according to FIG. 1, which is arranged in the interior of the housing 2 according to FIG. 1. On the top, the gas supply channel 10 enters in two areas of a spatially fixed base structure 15 of the component assembly 13. Both of these areas open between two gas conducting elements 14. Upper ends of the gas conducting elements 14 are mounted to the base structure 15 in a spatially fixed way, and one of the two electrodes 16 is mounted to each of their lower ends. The electrodes 16 are fixed to the lower ends of the gas conducting elements 14 by means of clamping shoes 22. Each of the two electrodes 16 is provided with a dielectric barrier 17. The linearly extending and parallel electrodes 16 are not spatially fixed with regard to the base structure 15. Instead, the gas conducting elements 14 are deformable in the scent of one-axis solid body joints. This allows for varying a lateral electrode distance 18 in that the electrodes 16 are swiveled about these solid body joints. Independently of the electrode distance 18 adjusted, the gas conducting elements 14 conduct the working gas, which enters between the gas conducting elements 14 via the gas supply channel 10, to the electrodes 16.

Figure 3:
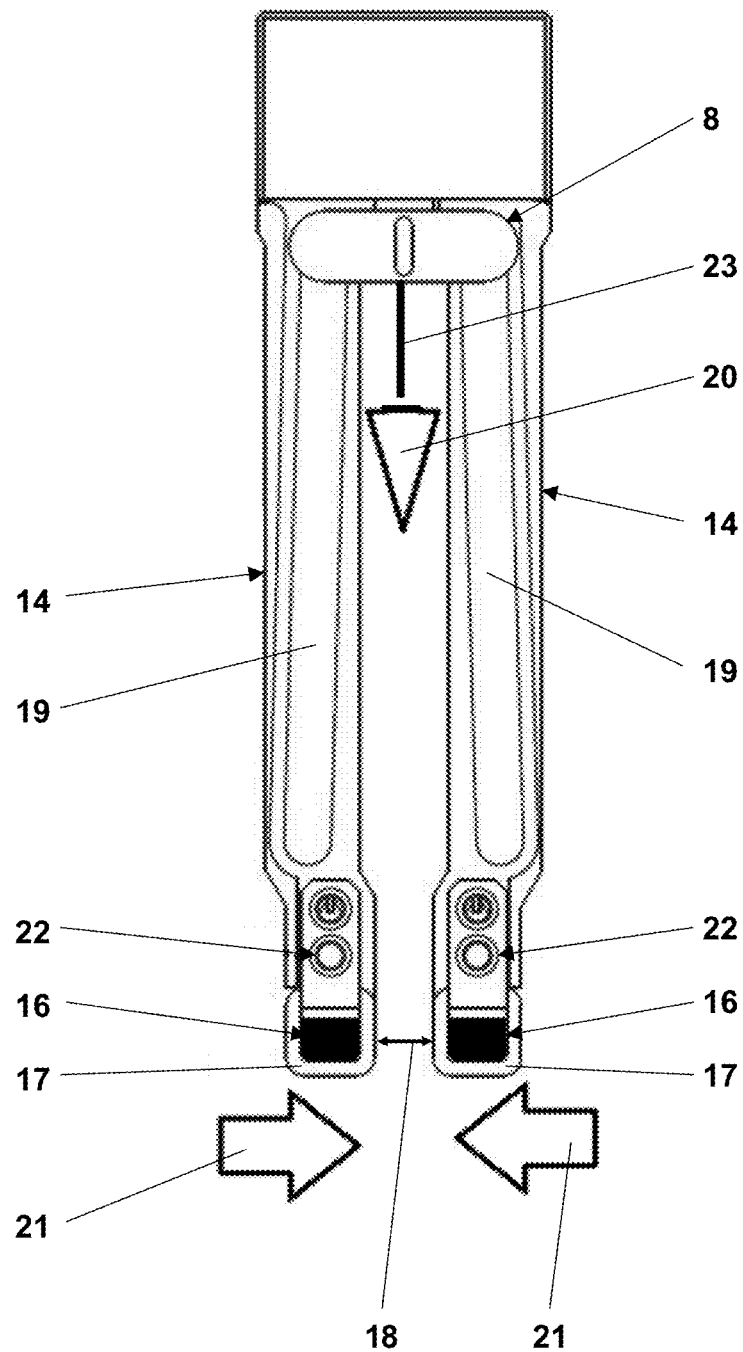
FIG. 3 is a side view of the component assembly according to FIG. 2 supplemented by a slider for adjusting a lateral electrode distance.

For varying the lateral electrode distance 18 in a controlled way, the sliders 8 are provided. Each of the sliders engages guide tracks 19 provided at side edges of the gas conducting elements 14 by means of actuating elements. FIG. 3 illustrates, how sliding the sliders 8 downwards in a direction of an arrow 20 brings together the at first diverting guide tracks 19 and thus also the electrodes 16 in direction of two arrows 21. In this way, the electrode distance 18 is reduced. The guide tracks 19 may, however, also have another, non-linear course so that the electrode distance 18 is not monotonically varied by sliding down the sliders 8. Further, by means of the sliders 8, a dielectric screen 23 is moved downwards up into the lateral electrode distance 18 between the electrodes 16.

Figure 4A:
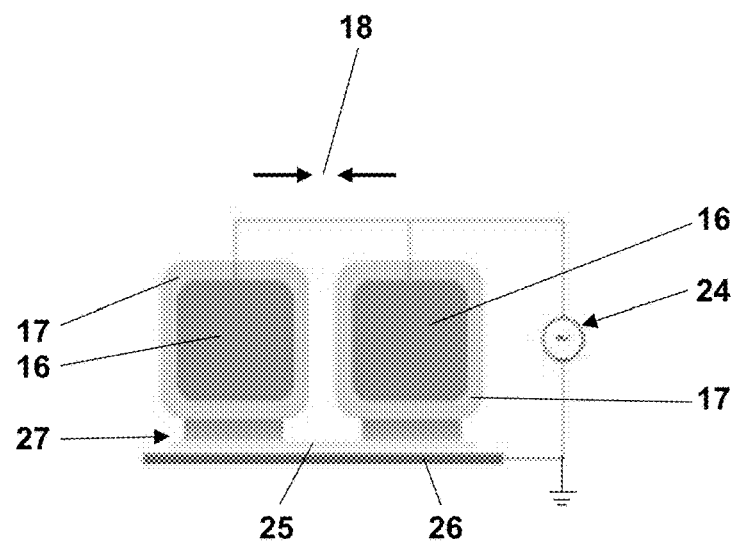
FIGS. 4A, 4B and 4C schematically illustrate three geometrically different discharge forms of dielectric barrier discharges generated by means of the plasma generator module according to FIGS. 1 to 3.
Figure 4B:
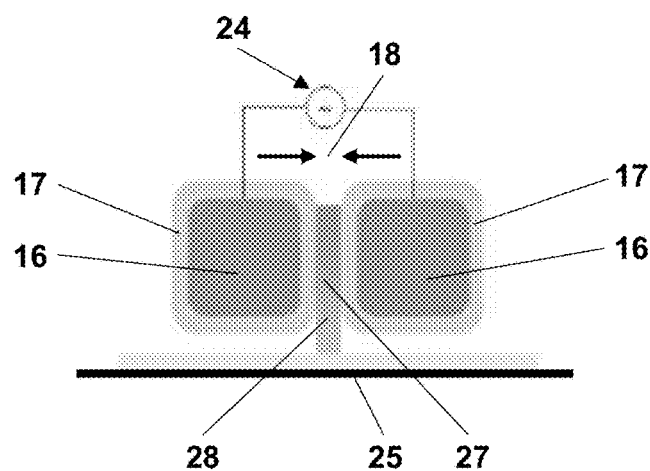
Figure 4C:
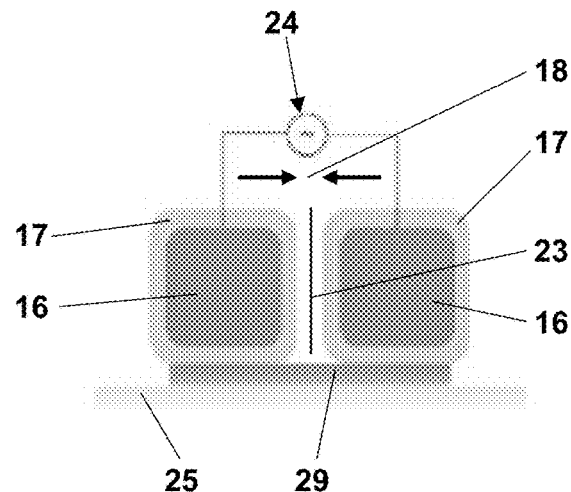

FIGS. 4A to 4C illustrate different discharge forms, which can be produced when generating a physical plasma at atmospheric pressure with the plasma generator module according to FIGS. 1 to 3. According to FIG. 4A, a same pole of an alternating high voltage of an alternating high voltage source 24 is connected to both electrodes 16 arranged at an arbitrary electrode distance 18. Then, the alternating high voltage is generated by the high voltage source 24 with regard to, for example, electric ground, and an object 25 to be treated is placed on an earthed support 26. Under these conditions, a direct dielectric barrier discharge 27 is generated between both electrodes 26 and the object 25.

According to FIG. 4B, at a comparatively small electrode distance 18, an alternating high voltage is applied between the electrodes 16 by means of the high voltage source 24, which results in a direct dielectric barrier discharge 27 between the electrodes 16. A physical plasma generated by the direct dielectric barrier discharge 27 is blown out as a plasma jet through the electrodes 16 onto the object 25 to be treated.

According to FIG. 4C, at a comparatively high electrode distance 18 or with the dielectric screen 23 being arranged between the electrodes 16, an alternating high voltage is applied between the electrodes 16 by means of the high voltage source 24. Here, the electrode distance 18 or the dielectric screen avoids that a direct dielectric barrier discharge occurs between the electrodes 16. Instead, a coplanar sliding discharge 29 is formed between each of the electrodes 16 and the object 25 to be treated. Wth an electrically conductive object 25, the discharge form of the dielectric barrier discharge may also be a direct dielectric barrier discharge here, in which the electrically conductive object 25 serves as an intermediate electrode.

In the plasma generator module 1 according to FIGS. 1 to 3, the optimum electrode distance for the respective discharge form according to FIG. 4A to 4C is adjustable. Further, the high voltage source 24 can be integrated or attached to the respective plasma generator module to switch it into that operation mode which is suitable for the respective discharge form with regard to the alternating high voltage provided. This switching of the high voltage source into the respective operation mode may be effected by sliding the slider 8.

Figure 5:
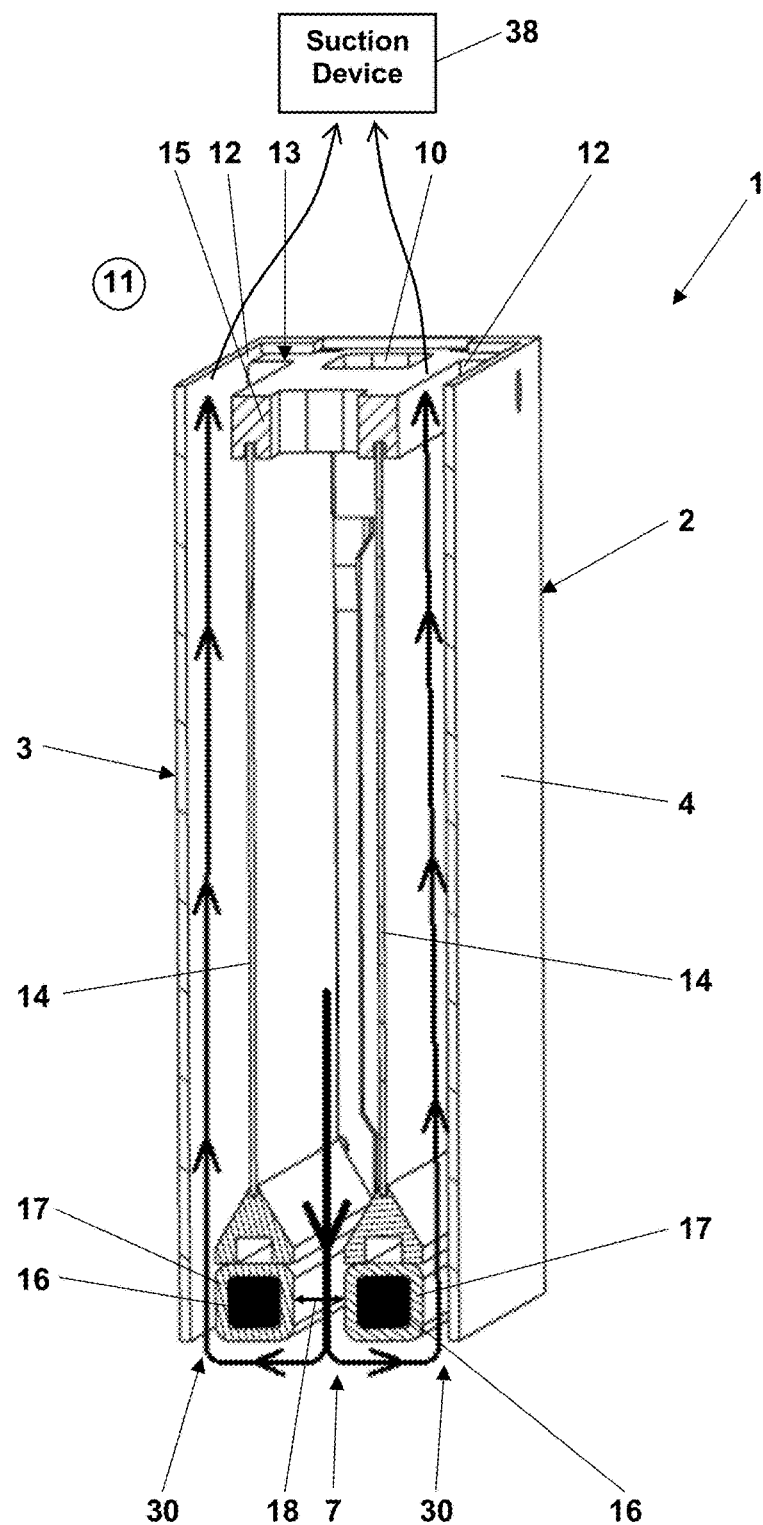
FIG. 5 is a section through a further embodiment of a plasma generator module of a module array according to the present invention.

In a section through another embodiment of the plasma generator module 1, FIG. 5, illustrates how the working gas air is guided through the module housing 2 and, in between, around the electrodes 16 at the underside 7 of the housing 2. Out of the surroundings 11, the working gas air gets between the gas conducting elements 14 via the gas supply channel 10. Guided by the gas conducting elements 14, the working gas gets between the electrodes 16 from above. Thus, the working gas passes through the electrode distance 18, and from there it flows around the electrodes 16 into the slit-shaped entrances 30 of the suction channel 12. Through the suction channel 12, the working gas is sucked off by the suction device 38 only schematically depicted in FIG. 5.

Figure 6:
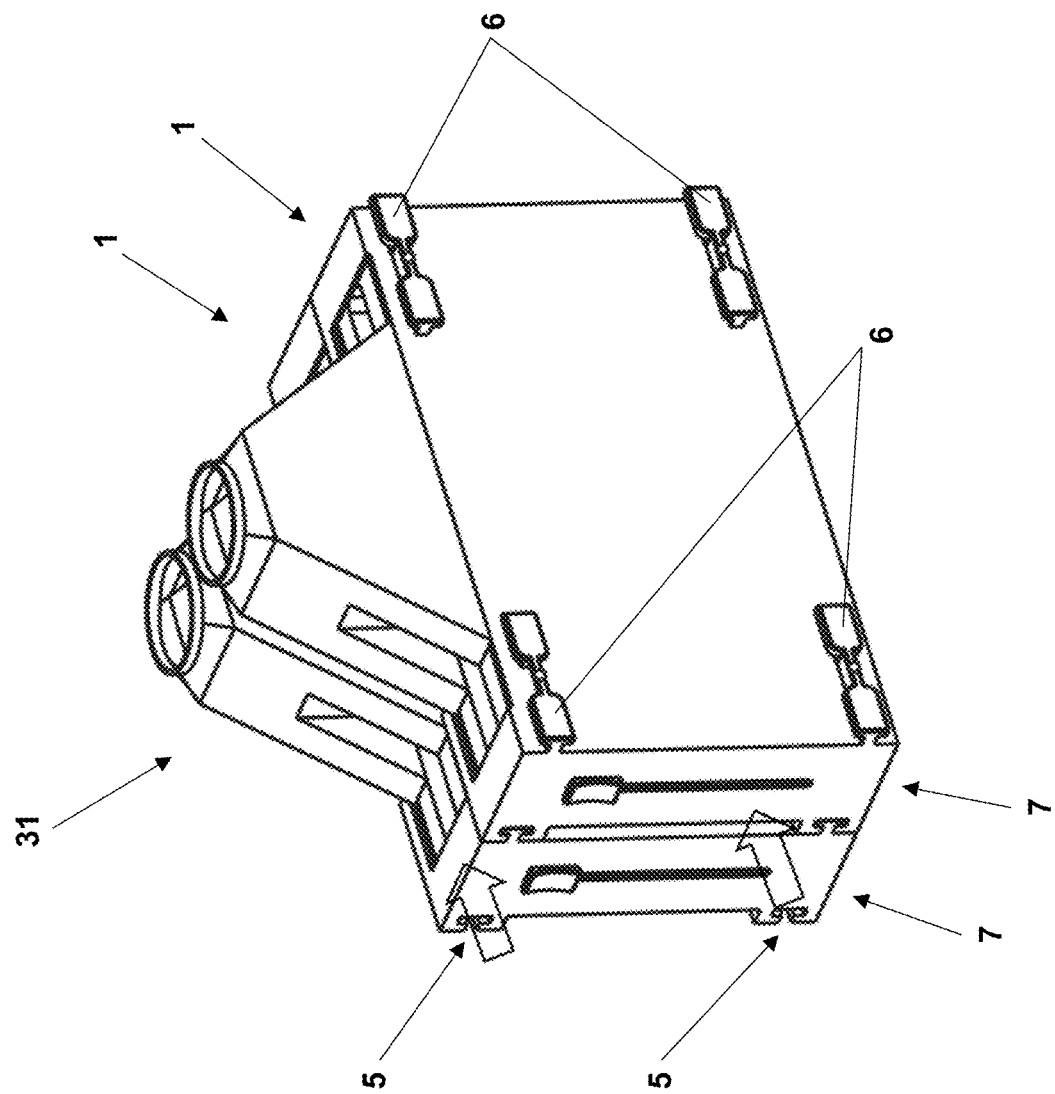
FIG. 6 illustrates a combination of two plasma generator modules according to FIG. 1.

FIG. 6 illustrates how a plurality of plasma generator modules 6 can be coupled by means of their fixation devices 5 and 6 in a direction transverse to the electrodes arranged at their undersides 7 to provide a module array 31 which is suitable for a plasma treatment of an object over a larger area.

Figure 7:
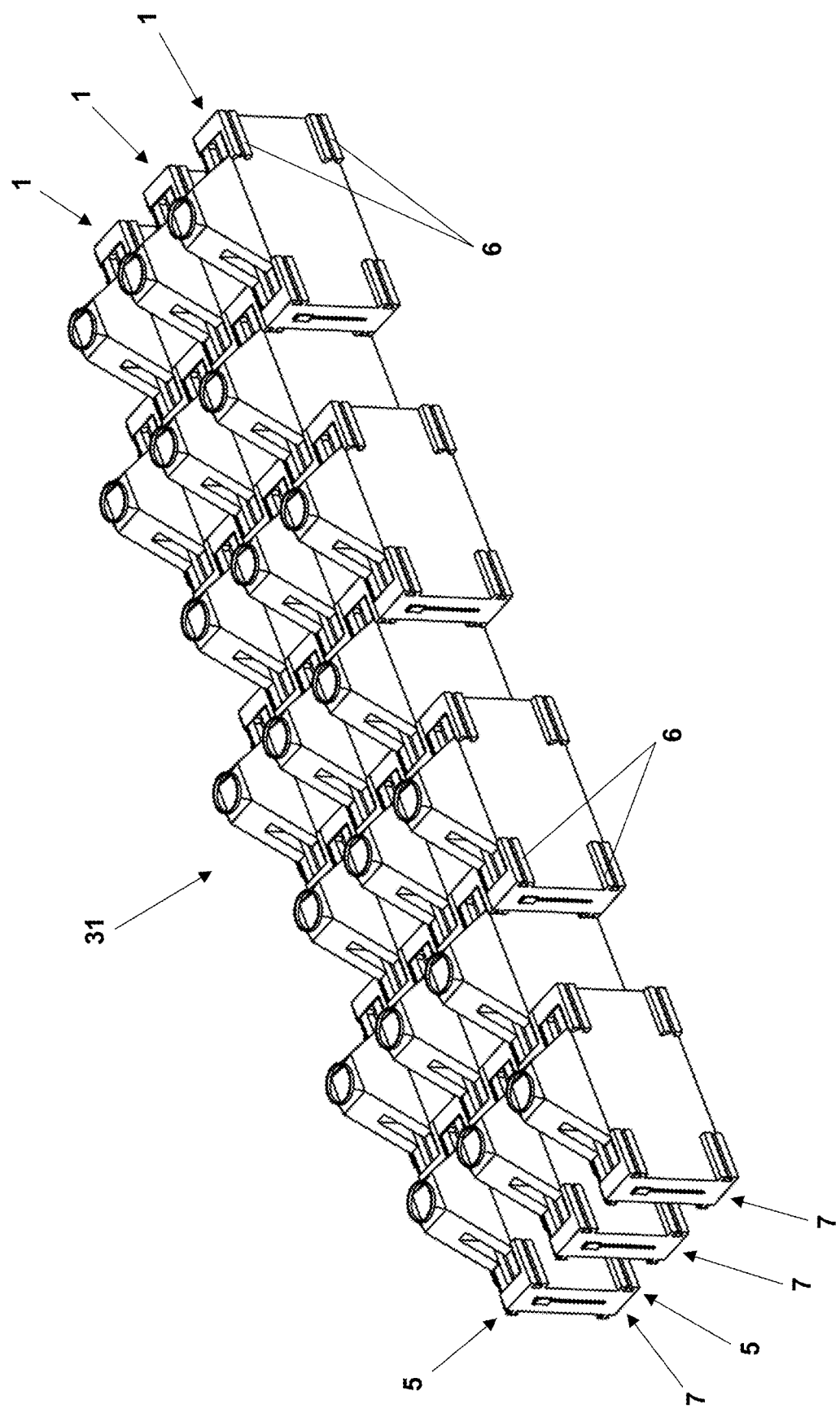
FIG. 7 illustrates the design of a module array according to the present invention consisting of a plurality of plasma generator modules according to FIG. 1.

FIG. 7 illustrates how, by means of the fixation devices 5 and 6, several plasma generator modules 6 are coupled in an offset way to provide a larger module array 31, in which the electrodes of the individual plasma generator modules 6 partially overlap in their direction of main extension. In the two dimensional module array 31 shown in FIG. 7, always three plasma generator modules 1 are arranged one behind the other in the direction transverse to the electrodes, and these three plasma generator modules 1 partially overlap with three neighboring plasma generator modules on both side. However, there may only be one see-saw or diagonal row of partially overlapping plasma generator modules 1. The partial overlap of the plasma generator modules ensures that the physical plasma at the underside of the module array 31 is generated over the entire width of the module array 31 without gaps.

Whereas FIGS. 6 and 7 show the formation of a module array 31 of same plasma generators modules 6 in the embodiment with adjustable electrode distance, such a module array 31 may also comprise plasma generator modules 6 of different embodiments to generate geometrically different discharge forms of the dielectric barrier discharge 27 at atmospheric pressure within the module array 31.

Figure 8:
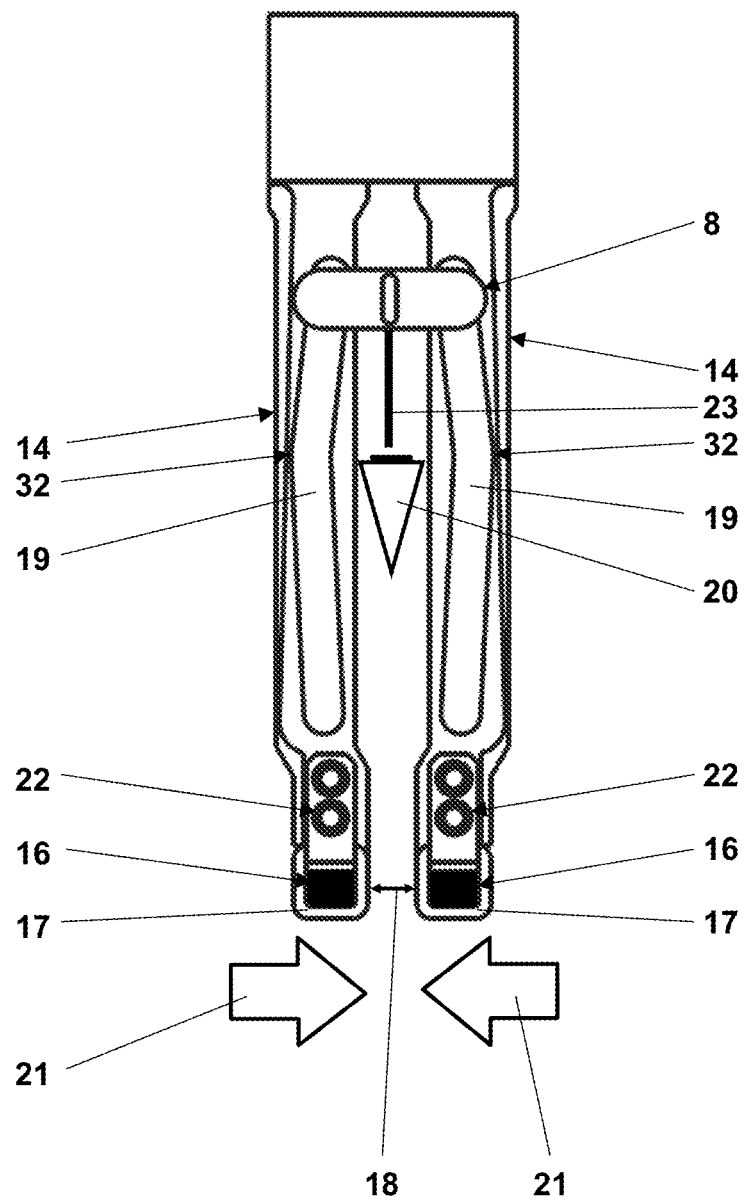
FIG. 8 is a side view corresponding to FIG. 3 of a component assembly of another embodiment of the plasma generator module according to FIG. 1.

The embodiment of the component assembly 13 depicted in FIG. 8 displays other courses of the guide tracks 19 so that the minimum electrode distance 18 is reached when the sliders 8 are located at the height of outwardly directed bends 32 of the guide rails 19. Thus, the electrode distance 18 is increased again when the dielectric screen 23 is moved between the electrodes 16 with the sliders 8 to provide optimum conditions for a coplanar sliding or surface discharge 29 according to FIG. 4C.

Figure 9:
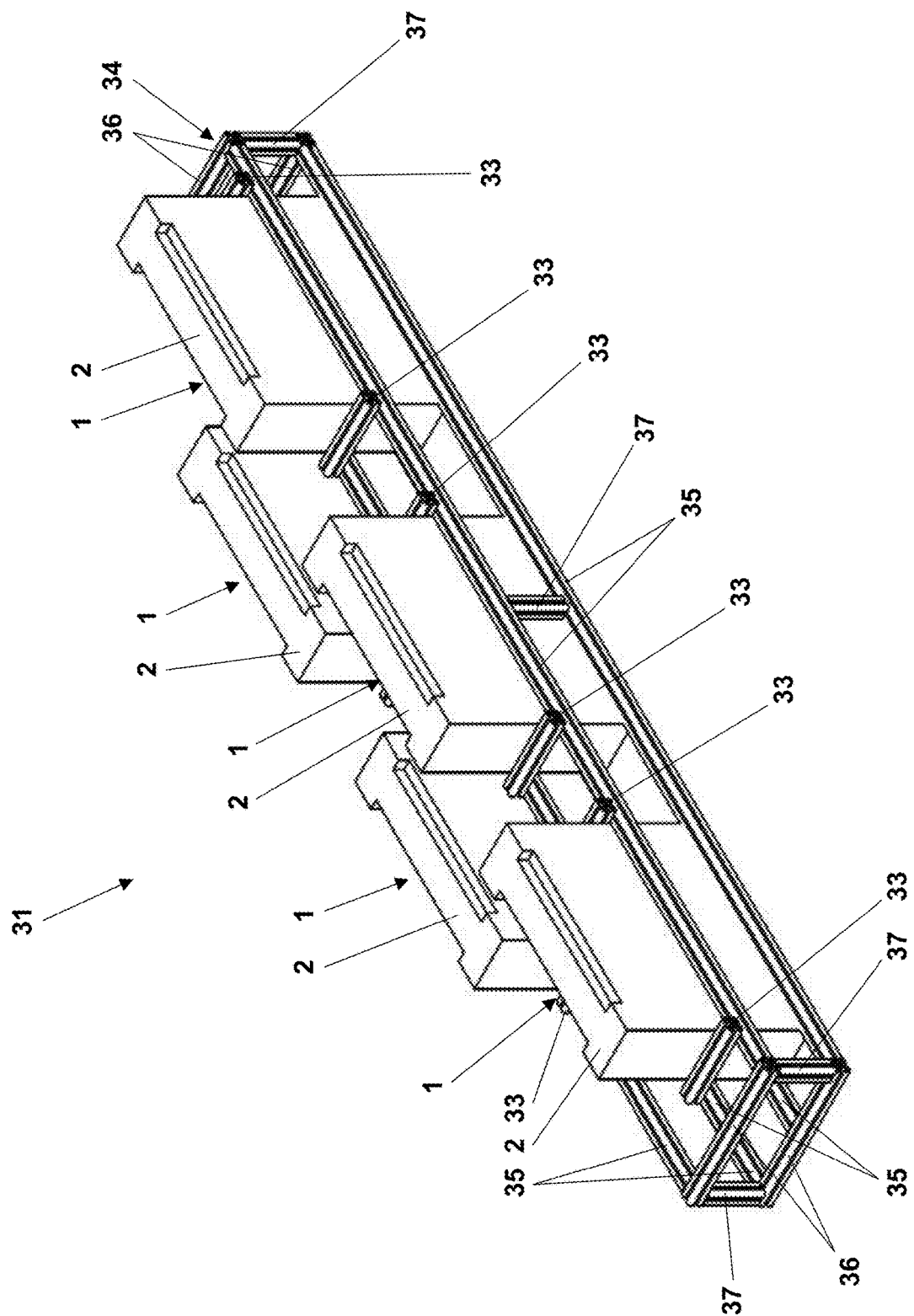
FIG. 9 illustrates the design of a module array according to the present invention consisting of a plurality of plasma generator modules with other fixation devices than depicted in FIGS. 1, 6 and 7.

FIG. 9 shows a module array 31 of plasma generator modules 1 with module housings 2 of a different design as compared to the module array according to FIGS. 6 and 7. According to FIG. 9, the fixation elements 33 provided at the module housings 2 are cross bars extending across the end faces of the module housings 2 at about half the height of the module housings 2. By means of these fixation devices 33, the plasma generator modules 1 are mounted in a module frame 34 constructed of longitudinal beams 35, cross beams 36 and vertical beams 37. By means of the longitudinal beams 35, the module housings 2 of the plasma generator modules 1 are guided in two parallel vertical planes. In the two vertical planes, the plasma generator modules 1 are arranged at offsets so that their electrodes partially overlap. With their fixation devices 23 the plasma generator modules 1 abut against the upper longitudinal beams 35. Along the longitudinal beams 35, the plasma generator modules 1 are freely movable until they abut against each other via their fixation devices 33.

Many variations and modifications may be made to the preferred embodiments of the invention without departing substantially from the spirit and principles of the invention. All such modifications and variations are intended to be included herein within the scope of the present invention, as defined by the following claims.

We claim:

1. A module array including a plurality of plasma generator modules configured for generating a physical plasma by dielectric barrier discharges at atmospheric pressure, wherein each of the plasma generator modules comprises
   two linearly extending electrodes extending parallel to each other at a lateral electrode distance, at least one of the two linearly extending electrodes being provided with a dielectric barrier;
   connection devices configured for connecting the two electrodes to a high voltage source;
   two flat gas-conducting elements configured for conducting a working gas between the two electrodes; and
   a module housing delimiting the respective plasma generator module laterally along the two electrodes and transversely to the two electrodes, and provided with fixation devices,
   wherein the module housings of the plasma generator modules of the plurality of plasma generator modules are fixed to one another or to a common module frame by their fixation devices, and
   wherein the module housings of the plasma generator modules of the plurality of plasma generator modules are arranged
      side by side both in a first direction along and in a second direction transverse to the two electrodes of the plurality of plasma generator modules, and
      in an offset way such that the two electrodes of the plurality of plasma generator modules partially overlap in the direction along the two electrodes.

2. The module array of claim 1, wherein the fixation devices are provided at lateral walls of the module housings of the plurality of plasma generator modules, the lateral walls extending along the two electrodes of the respective plasma generator module.

3. The module array of claim 1, wherein one of the two electrodes of at least one of the plurality of plasma generator modules is mounted to a first end of one of the two gas-conducting elements of the at least one of the plurality of plasma generator modules in such a way that the one of the two electrodes, together with the first end of the one of the two gas-conducting elements is movable with regard to the other of the two electrodes and the other of the two gas-conducting elements in the direction of the electrode distance such that the electrode distance of the at least one of the plurality of plasma generator modules is adjustable to different values.

4. The module array of claim 3, wherein the one of the two gas-conducting elements, with its second end opposite to its first end, is mounted to a base structure of the respective plasma generator module via a swivel joint or a solid body joint having one swivel axis parallel to the one of the two electrodes of the at least one of the plurality of plasma generator modules.

5. The module array of claim 3, wherein the other of the two electrodes of the at least one of the plurality of plasma generator modules is mounted to a first end of the other of the two gas-conducting elements in such a way that the other of the two electrodes, together with the first end of the other of the two gas-conducting elements is movable with regard to the one of the two electrodes and the one of the two gas-conducting elements in the direction of the electrode distance such that the electrode distance of the at least one of the plurality of plasma generator modules is adjustable to different values.

6. The module array of claim 5, wherein at least one of the plurality of plasma generator modules comprises two sliders, which engage side edges of the two gas-conducting elements of the at least one of the plurality of plasma generator modules, and which, when being slid along a guide extending transversely to the two electrodes of the at least one of the plurality of plasma generator modules, alter the electrode distance of the at least one of the plurality of plasma generator modules.

7. The module array of claim 6, wherein at least one of the plurality of plasma generator modules comprises a dielectric screen, which is coupled to the sliders of the at least one of the plurality of plasma generator modules and transferable forth and back between an inactive position located between the gas-conducting elements of the at least one of the plurality of plasma generator modules and an active position located between the two electrodes of the at least one of the plurality of plasma generator modules.

8. The module array of claim 1, wherein at least one of the plurality of plasma generator modules comprises a dielectric screen, which is transferable forth and back between an inactive position located between the gas-conducting elements of the at least one of the plurality of plasma generator modules and an active position located between the two electrodes of the at least one of the plurality of plasma generator modules.

9. The module array of claim 1, wherein each of the plurality of plasma generator modules comprises its own high voltage source, which is a part of the respective plasma generator module.

10. The module array of claim 9, wherein the high voltage sources of the plurality of plasma generator modules are connectable to an external low voltage source via low voltage connectors and low voltage lines, only.

11. The module array of claim 1, wherein at least one of the plurality of plasma generator modules comprises a suction channel having a slit-shaped entrance extending adjacent and parallel to one of the two electrodes of the at least one of the plurality of plasma generator modules at a side of the one of the two electrodes facing away from the other of the two electrodes, wherein the suction channel extends over one of the two gas-conducting elements connected to the one of the two electrodes, on an outer side of the one of the two gas-conducting elements facing away from the other of the two gas-conducting elements.

12. The module array of claim 11, wherein the at least one of the plurality of plasma generator modules comprises a further suction channel having a further slit-shaped entrance extending adjacent and parallel to the other of the two electrodes of the at least one of the plurality of plasma generator modules at a side of the other of the two electrodes facing away from the one of the two electrodes, wherein the further suction channel extends over the other of the two gas-conducting elements connected to the other of the two electrodes, on an outer side of the other of the two gas-conducting elements facing away from the one of the two gas-conducting elements.

13. The module array of claim 11, wherein a suction device is connected to the suction channel of the at least one of the plurality of plasma generator modules such that the working glass conducted by the gas-conducting elements gets between the two electrodes, passes through the electrode distance and from there, around the at least one of the two electrodes gets into the slit-shaped entrance of the suction channel of the at least one of the plurality of plasma generator modules, through which it is sucked in by the suction device.

14. The module array of claim 13, wherein at least one of the plurality of plasma generator modules comprises a working gas supply channel, which is spatially fixed with regard to the base structure of the at least one of the plurality of plasma generator modules and leads between the two gas-conducting elements of the at least one of the plurality of plasma generator modules.

15. The module array of claim 14, wherein the working gas supply channel of the at least one of the plurality of plasma generator modules leads air out of a surrounding of the at least one of the plurality of plasma generator modules as the working gas between the gas conducting elements of the at least one of the plurality of plasma generator modules.

16. The module array of claim 1, wherein different ones of the plurality of plasma generator modules are configured for generating geometrically different discharge forms of the dielectric barrier discharges at atmospheric pressure in that they differ in values of their electrode distances.

17. The module array of claim 1, wherein the high voltage source, for generating geometrically different discharge forms of the dielectric barrier discharges, is switchable between different operation modes, in which the high voltage source applies different high voltages to the two electrodes of at least one of the plurality of plasma generator modules.

18. The module array of claim 1, wherein the high voltage source, for generating geometrically different discharge forms of the dielectric barrier discharges, is switchable between a first operation mode, in which the high voltage source applies a same alternating high voltage to the two electrodes with regard to electric earth, and a second operation mode, in which the high voltage source applies an alternating high voltage between the two electrodes of the respective one of the plurality of plasma generator modules.

19. The module array of claim 1, wherein the plurality of plasma generator modules is configured for generating spatially one next to the other at least two geometrically different discharge forms of the dielectric barrier discharges at atmospheric pressure, wherein the different discharge forms at least two discharge forms from the following group of discharge forms direct dielectric barrier discharges between the two electrodes of the respective one of the plurality of plasma generator modules, on the one hand, and an object positioned opposite to the two electrodes of the respective one of the plurality of plasma generator modules, on the other hand, direct dielectric barrier discharges between the two electrodes of the respective one of the plurality of plasma generator modules, which generate a plasma blown as a plasma jet onto an object positioned opposite to the two electrodes of the respective one of the plurality of plasma generator modules, and direct dielectric barrier discharges and coplanar surface discharges between one of the two electrodes of the respective one of the plurality of plasma generator modules and an object positioned opposite to the two electrodes as well as between the object and the other of the two electrodes of the respective one of the plurality of plasma generator modules.

20. The module array of claim 1, wherein at least one of the plurality of plasma generator modules is configured for generating temporarily one after the other at least two geometrically different discharge forms of the dielectric barrier discharges at atmospheric pressure, wherein the different discharge forms include at least two discharge forms from the following group of discharge forms

- direct dielectric barrier discharges between the two electrodes of the respective one of the plurality of plasma generator modules, on the one hand, and an object positioned opposite to the two electrodes of the respective one of the plurality of plasma generator modules, on the other hand,
- direct dielectric barrier discharges between the two electrodes of the respective one of the plurality of plasma generator modules, which generate a plasma blown as a plasma jet onto an object positioned opposite to the two electrodes of the respective one of the plurality of plasma generator modules, and
- direct dielectric barrier discharges and coplanar surface discharges between one of the two electrodes of the respective one of the plurality of plasma generator modules and an object positioned opposite to the two electrodes as well as between the object and the other of the two electrodes of the respective one of the plurality of plasma generator modules.

* * * * *